United States Patent [19]

Wilkinson et al.

[11] Patent Number: 4,666,917

[45] Date of Patent: May 19, 1987

[54] SUBSTITUTED ACRIDINE DERIVATIVES USEFUL AS MODULATORS OF THE IMMUNE SYSTEM

[75] Inventors: Raymond G. Wilkinson, Montvale, N.J.; Yang-I Lin, Nanuet, N.Y.

[73] Assignee: American Cyanamid Company, Stamford, Conn.

[21] Appl. No.: 669,916

[22] Filed: Nov. 9, 1984

[51] Int. Cl.$^4$ ..................... A61K 31/47; C07D 219/06
[52] U.S. Cl. ..................... 514/297; 514/237; 514/240; 544/126; 546/104
[58] Field of Search ................ 546/104; 514/297, 240, 514/237; 544/125, 126

[56] References Cited

U.S. PATENT DOCUMENTS

| | | | |
|---|---|---|---|
| 1,727,480 | 9/1929 | Mietzsch | 546/104 |
| 2,881,210 | 4/1959 | Zaugg et al. | 548/473 |
| 3,008,963 | 11/1961 | Mathes et al. | 546/340 |
| 3,740,403 | 6/1973 | Murdock | 546/104 |
| 4,273,891 | 6/1981 | Pindar et al. | 568/674 |
| 4,314,061 | 2/1982 | Murdock et al. | 544/80 |

FOREIGN PATENT DOCUMENTS 0490418  1/1930  Fed. Rep. of Germany ...... 546/104

OTHER PUBLICATIONS

Parikh, et al., J. Am. Chem. Soc., vol. 89(21) pp. 5505-5507 (1967).
Wegler, et al., J. Chemical Abstracts, vol. 44, 1940a (1950).
Hess, et al., J. Med. Chem., vol. 18, No. 3, pp. 320-321 (1975).
Chemical Abstracts Tenth Collective Index, General Subjects, p. 11628GS, "Hydroxymethylation" (1982).
Konyukhov, et al., Chemical Abstracts, vol. 90, 151952w (1979).

*Primary Examiner*—Donald G. Daus
*Assistant Examiner*—Diana G. Rivers
*Attorney, Agent, or Firm*—Gregg C. Benson; Robert P. Raymond

[57] ABSTRACT

This invention concerns novel substituted acridine compounds which are useful as modulators of the immune system in warm-blooded animals.

20 Claims, No Drawings

SUBSTITUTED ACRIDINE DERIVATIVES USEFUL AS MODULATORS OF THE IMMUNE SYSTEM

BACKGROUND OF THE INVENTION

1. Field of the Invention

This invention is concerned with new compounds of the formula:

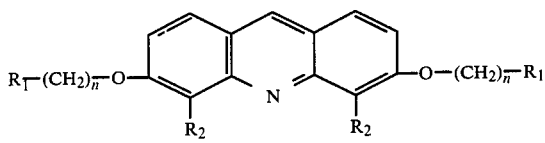

wherein n is an integer 2 or 3; $R_1$ is selected from the group consisting of piperidinyl, —N[alkyl($C_1$–$C_5$)]$_2$, pyrrolidino and morpholino; $R_2$ is selected from the group consisting of formyl, hydroxymethyl, aminomethyl and

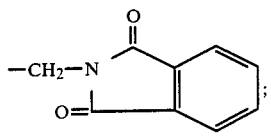

together with the pharmaceutically acceptable salts thereof.

In a preferred embodiment, this invention is concerned with new compounds of the formula:

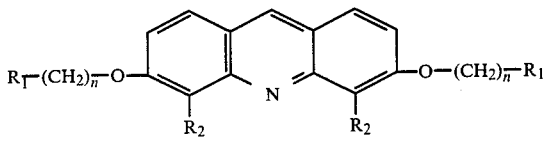

wherein n is 2; $R_1$ is selected from the group consisting of piperidinyl and —N[$C_2H_5$]$_2$; $R_2$ is selected from the group consisting of formyl, hydroxymethyl, aminomethyl and

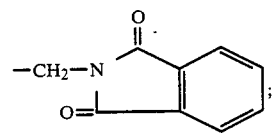

together with the pharmaceutically acceptable salts thereof.

In addition, this invention is concerned with a method of treating the immune response system in a warm-blooded animal which comprises administering to said animal an effective amount of a compound selected from those of the above formulas in association with a pharmaceutically acceptable carrier, adjuvant or diluent.

2. Description of the Prior Art

The use of immunomodulants and chemotherapeutic adjuvants constitutes a new therapeutic approach to the treatment of immune deficiences and cancer and is based on the concept that there are distinctive antigens in or on most tumor cells (embryonal or transplantation antigens) that distinguish them from normal host cells. A majority of tumor immunologists favor the view that potentially malignant cells constantly arise but, because of their "foreigness", are normally eliminated by a competent humoral and cellular immune system. Occasionally, however, tumor cells escape this immune surveillance and continue to reproduce and cancer results. The reason for the failure of the normally efficient immune surveillance mechanisms is not fully understood but it is thought that the immume system becomes less effective with increasing age. It is depressed in certain genetic immuno-deficiency diseases, in various bacterial, fungal or viral infections and in patients undergoing immunosuppressive therapy. The growth of the neoplasm itself, as well as the various therapeutic modalities designed to treat the disease, e.g., cytotoxic chemotherapy and radiation, leads to a still greater depression of host resistance and results in an increased susceptibility to both exogenous and endogenous infections and perhaps accounts for the re-initiation of tumor growth and metastasis which frequently follows treatment-induced tumor remission.

If depression of the immune system can result in the growth of malignancies, regulation of any facet of the immune response may help the host to eliminate residual cancer cells. therefore, it is desirable to search for chemical agents (i.e., immunoregulants) capable of restoring and stimulating host immune defense mechanisms in order to overcome the deficiencies which account for susceptibility to disease and failure to eradicate the cancer. Such immunoregulating agents would likely be incapable of arresting the growth of a larger tumor but their clinical utility would derive from their capacity to enhance normal immune surveillance mechanisms in patients whose tumor burden has been reduced by surgical, radiotherapeutic or chemotherapeutic methods.

Experimental studies in animals have demonstrated the antitumor potential of a number of immunoregulants including live organisms of bacillus Calmette-Guerin (BCG), heat-killed cells of *Corynebacterium parvum*, polynucleotides and the anthelmintic drug, levamisole. These substances have been shown to stimulate cellular immunity and to produce tumor regression. Some successes have been claimed in early clinical trials with BCG against malignant melanoma and acute leukemia and with levamisole against lung cancer and breast cancer. Although the antitumor effects produced by these agents have been promising, significant therapeutic benefits have yet to be realized. Since this is a new therapeutic approach, new drugs and methods of treatment must receive careful clinical evaluation in order to reveal their full potential.

Modern research is directed to the discovery of a drug similar to, but more potent than, known immunoregulants such as levamisole that would be effective in the eradication of tumor cells when used in conjunction with standard therapeutic measures. Stimulators of host resistance may be detected in animal models that can, in fact, detect both immunostimulators and anticancer agents. Mice are put in a condition simulating immunodepression common to cancer patients. This is accomplished by infecting mice with a leukemia virus which produces both leukemia and a disease-related immunodepression. Effective drugs are recognized by their ability to restore or enhance the antibody response in the experimental mice, or to inhibit tumor progression.

Certain synthetic and naturally derived compounds have the ability to induce high levels of circulating interferon. Among these are bacterial endotoxins, intact bacteria and viruses, transplantable tumor cells and a variety of high and low molecular weight synthetic compounds such as poly I:C, tilorone and pyran copolymer [W. E. Stewart, The Interferon System, Springer-Verlag, Wein, N.Y. (1979)]. Interferon has a major regulatory function in modulating cellular and humoral immune responses. Interferon, and inducers of interferon, "activate" macrophages to destroy tumor and virus infected cells, stimulate populations of immune cells to secrete lymphokines, protect against lethal infection by viruses and some bacterial species and stimulate the level of natural killer lymphocyte (NK-cell) activity in animals [Herberman, R. B. and Holden, H. T., Natural Cell-Mediated Immunity, Adv. Cancer Res., 27, 305–377 (1978) and Natural Killer Cells as Antitumor Effector Cells, J. Nat. Cancer Inst., 62 (3), 441–445 (1979)]. NK-cells play a major roll in immune surveillance in that they mediate the destruction of virus infected cells and a wide variety of syngeneic, allogenic and xenogeneic tumor cells when tested in vitro (Herberman, R. B. and Holden, H. T. vide supra). The role of NK-cells in protecting animals against virus infection appears certain.

It is an ojbect of this invention to provide compounds which are authentic modulators of humoral and cellular immunity (the immune system) in warm-blooded animals. It is a particular object of this invention to provide compounds which induce high levels of circulating interferon, restore antibody production in immunosuppressed warm-blooded animals, protect against lethal virus infection and stimulate NK-cell cytotoxicity for tumor cells.

It is a further object of this invention to provide a method of treating the immune system in a warm-blooded animal with compounds of this invention. More especially, it is an object of this invention to provide a method of treating the immune system in a warm-blooded animal with compounds of this invention in association with a pharmaceutically acceptable carrier, adjuvant or diluent.

SUMMARY OF THE INVENTION

The compounds of this invention may be prepared in accordance with the following flowcharts and descriptions.

FLOWCHART A

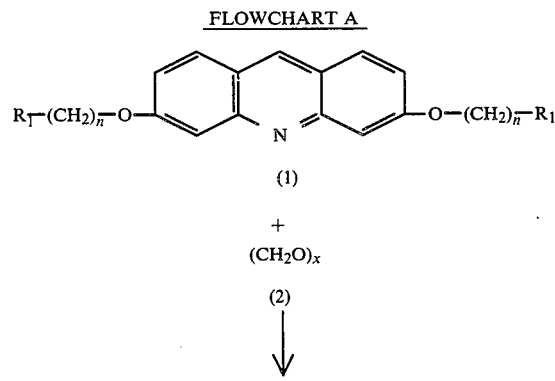

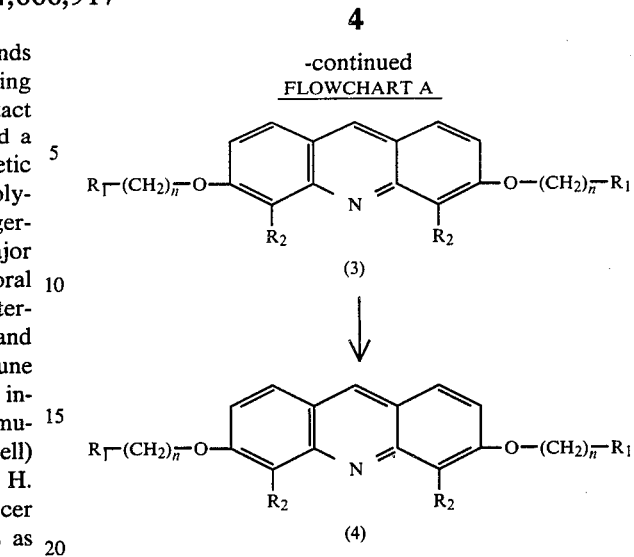

In accordance with Flowchart A, a 3,6-bis(substituted)acridine (1), where $R_1$ and n are as described above, in concentrated sulfuric acid is reacted with paraformaldehyde (2), where x is an integer greater than 1, for about ½ to about one hour then precipitated in ether, giving (3), where $R_2$ is —$CH_2OH$. The resulting solid is dissolved in dimethyl sulfoxide, triethylamine is added and the mixture reacted with sulfur trioxide-pyridine complex for about 1 to about 4 hours giving (4) where $R_1$ and n are as described above and $R_2$ is formyl.

FLOWCHART B

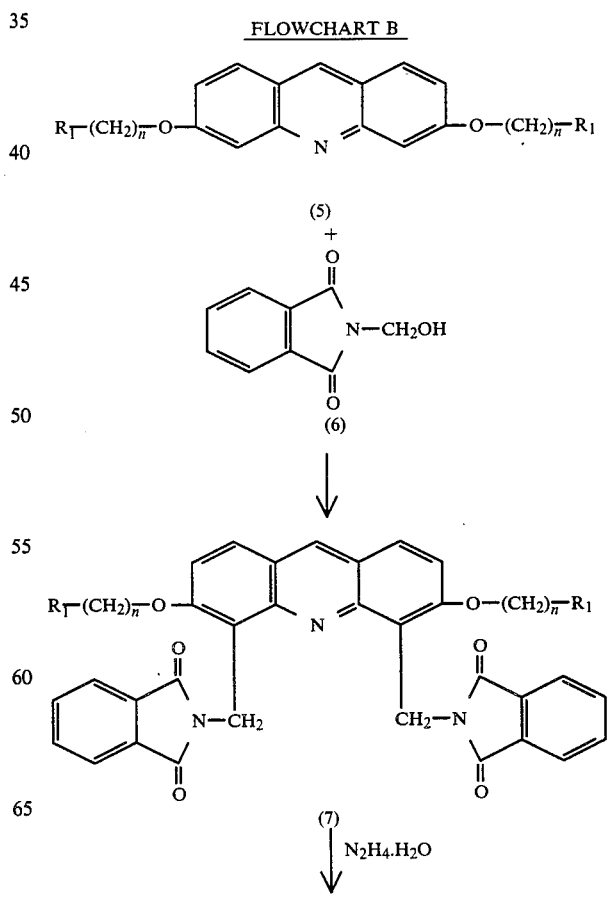

-continued
FLOWCHART B

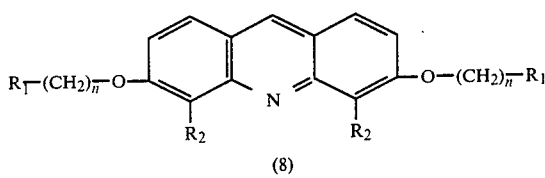

(8)

In accordance with Flowchart B, a 3,6-bis(substituted)acridine (5), where $R_1$ and n are as described above, is dissolved in concentrated sulfuric acid and reacted with hydroxymethyl phthalimide (6) for about 12 to about 24 hours to give (7) which is then reacted with hydrazine hydrate in ethanol at reflux for about 2 to about 4 hours giving (8), where $R_1$ and n are as described above and $R_2$ is aminomethyl.

The compounds of the present invention have been examined in a variety of murine model systems designed to evaluate their ability to restore or enhance cellular and humoral immune responses.

In the Rauscher virus model, the ability to produce antibodies to a complex antigen (sheep red blood cells) is severely depressed. The compounds of this invention partially restore functioning of this complex immune system and stimulate antibody production to more normal levels.

DETAILED DESCRIPTION OF THE INVENTION

The active compounds and novel compositions of the present invention are active as immune modulators when tested according to the following procedures:

(A)

Inhibition of Splenomegaly and Restoration of Antibody Formation in Mice with Rauscher Virus-Induced Leukemia Injection of BALB/c mice with Rauscher leukemia virus (RLV) is characterized by: (1) a rapidly developing viremia, (2) suppression of the primary antibody response to antigens administered a few days after virus infection, (3) a progressive enlargement of the spleen (splenomegaly) and (4) death resulting from splenic rupture and hemorrhage. The protocol used to infect BALB/c mice with RLV and to test drugs for anticancer and/or immunostimulating activity is as follows:

Day 0: Inject 0.2 ml intraperitoneally (IP) of a 20% (w/v) RLV-infected spleen cell extract into groups of 5 BALB/c mice. The spleen cell extract is prepared from mice infected with RLV 21 days previously.

Day +6, +7, +8: Test compounds are administered orally in 0.5 ml of normal saline containing 0.2% Nobel agar on days +6, +7 and +8.

Day +7: Inject 0.5 ml of a thrice saline washed 10% suspension of sheep red blood cells (S-RBC).

Day +14: Bleed mice from the retro-orbital sinus; pool blood from each group. Sacrifice mice, remove and weigh spleens. Serum, harvested from pooled blood of each group of mice is stored at 4° C. for 24 hours. Hemagglutinin tests are performed by standard procedures using a microtiter technique. Acceptable hemagglutinin titer for leukemic (immunosuppressed) mice is $\leq 1:128$. The positive control compound is Poly I:C (polyinosinic acid:polycytidylic acid) administered intraperitoneally on days +6, +7 and +8. Acceptable positive control hemagglutinin titers are 4-fold higher than the titers obtained in leukemic control mice. Average spleen weights of drug treated groups of mice are compared to the average spleen weight of the RLV-infected, placebo treated mice.

Typical compounds of this invention are active in this test in that they produce a 50% or greater reduction in splenomegaly and a 4-fold or higher increase in hemagglutinin titer to sheep-RBC's relative to the placebo treated, RLV-infected control mice. Results of this test appear in Tables I and II.

TABLE I

Rauscher Virus-Induced Leukemia-Percent Reduction in Splenomegaly

| Drug Treatment | Dose (mg/kg) | % Reduction |
| --- | --- | --- |
| 2,2'-[[3,6-bis[2-(1-piperidinyl)-ethoxy]-4,5-acridinediyl]bis(methylene)]bis-1H—isoindol-1,3(2H)—dione, sulfate (2:5) | 400 | 77 |
| 3,6-bis[2-(diethylamino)ethoxy]-4,5-acridinedimethanol | 400 | 80 |
| 2,2'-[[3,6-bis[2-diethylamino)-ethoxy]-4,5-acridinediyl]bis(methylene)]bis-1H—isoindol-1,3(2H)—dione | 400 | 73 |
| Control, 1,4-bis[(2-aminoethyl)-amino]-5,8-dihydroxyanthraquinone, dihydrochloride (U.S. Pat. No. 4,197,249) | 2 | 85 |

TABLE II

Antibody Restoration in Mice with Rauscher Virus-Induced Leukemia

| Drug Treatment | Dose (Oral) (mg/kg) | Serum Hemagglutinin Titer Saline Control Titer (Fold Increase) |
| --- | --- | --- |
| 3,6-bis[2-(diethylamino)ethoxy]-4,5-acridinedimethanol | 400 | 32 |
| 2,2'-[[3,6-bis[2-(diethylamino)-ethoxy]-4,5-acridinediyl]bis-(methylene)]bis-1H—isoindol-1,3(2H)—dione | 400 | 4 |
| Control, Poly I:C | 10 | 4 |

(B)

Induction of Circulating Interferon in Mice

Groups of six normal BDF$_1$ male mice were administered a single dose of test compound by the oral, intravenous (IV), intraperitoneal (IP) or subcutaneous (SC) route. Six or eighteen hours later, mice were bled from the retro-orbital sinus and the serum from each group was pooled. Control mice received a 0.2% Noble agar placebo instead of test compound. Assays of serum interferon were carried out using the semimicroassay of W. E. Stewart (1). The interferon titer of each serum was defined as the reciprocal of the highest dilution of serum that produced a 50% reduction in cytopathic effects of vesicular stomatitis virus (VSV) on monolayers of mouse L-929 cells. The high levels of serum interferon induced in mice, following administration of test compounds, are presented in Table III below.

References to this animal model test system are:
(1) The Interferon System. Stewart, W. E., Springer-Verlag, Wein, N.Y. 1979.
(2) Inteferon and Interferon Inducers. Stringfellow, D. A., Marcel Dekker, Inc., New York, 1980.

TABLE III

Induction of Circulating Interferon in BDF₁ Mice

| Compound | Dose* (mg/kg) | Route | Time After Drug Administration (Hours) | Serum** Interferon Titer |
|---|---|---|---|---|
| 0.2% Noble agar | — | Oral | 18 | >100<320 |
| 3,6-bis[2-(diethylamino)ethoxy]-4,5-acridinedimethanol | 400 | Oral | 24 | 2100 |
| Control, 3,6-bis(2-piperidinoethoxy)-acridine, trihydrochloride (U.S. Pat. No. 4,314,061) | 400 | Oral | 24 | 700 |

*BDF₁ male mice received a single dose of test compound, in normal saline, at zero time.
**Reciprocal of serum dilution producing a 50% reduction in cytopathic effects of vesicular stomatitis virus in murine L-929 cells.

(C)

Effect of Dose Interval Time on Efficacy of Drugs Against Lethal Virus Challenge of Mice with an Interferon-Sensitive Virus, Columbia SK Swiss female mice received a single oral dose of test compound or 3,6-bis(2-piperidinoethoxy)acridine, trihydrochloride (U.S. Pat. No. 4,314,061) as a control compound one day prior to lethal subcutaneous virus challenge on day zero with an LD₉₅ of Columbia SK virus. The test drugs were suspended in 1.0 ml of 0.2% aqueous agar solution. The test was evaluated 7 days after virus infection. Non-treated controls died with a mean survival time of 5.4 days after infection. The results of this test on typical compounds of this invention appear in Table IV.

TABLE IV

Effect of Dose Interval Time on Efficacy of Drugs Against Lethal Challenge of Mice with an Interferon-Sensitive Virus, Columbia SK

| Oral Treatment Time Relative to Virus Challenge (Days) | Number Survivors/Number Treated | Control Compound (400 mg/kg) | Non-treated Controls |
|---|---|---|---|
| 1 day prior | 2,2'-[[3,6-bis[2-(1-piperidinyl)ethoxy]-4,5-acridinediyl]bis(methylene)]bis-1H—isoindol-1,3(2H)—dione, sulfate (2:5)(400 mg/kg)<br>2/20 | 16/20* | 2/20 |
| 1 day prior | 3,6-bis[2-(diethylamino)ethoxy]acridinedimethanol (400 mg/kg)<br>17/20* | 16/20* | 2/20 |
| 1 day prior | 2,2'-[[3,6-bis[2-(diethylamino)ethoxy]-4,5-acridinediyl]bis(methylene)bis-1H—isoindol-1,3(2H)—dione (400 mg/kg)<br>4/20 | 16/20* | 2/20 |

*Indicates significant increase in survival ratio compared to non-treated controls (p < .01).

The compounds of this invention are authentic modulators of humoral and cellular immunity in mice. The compounds induce high levels of circulating interferon, restore antibody production in immunosuppressed mice, protect against lethal virus infection and stimulate NK-cell cytotoxicty for tumor cells.

It should be understood that this invention relates to modulation of the immune system in warm-blooded animals. Reference herein to animal systems using mice as test subjects is not to be construed as limiting the scope of this invention but rather as illustrative of the efficacy of the compounds of this invention.

It also should be understood that the compounds of this invention used in the above tests and the parameters of the test systems are illustrative and are not to be construed as limiting this invention.

The method of modulating the immune system of a warm-blooded animal which comprises administering to said animal an affective amount of a compound of this invention employs methods of treatment, dosage levels and requirements which are well-recognized in the art and may be chosen by those of skill in the art from available methods and techniques.

In order to more fully illustrate the nature of this invention and the manner of practicing same, the following examples are presented. It should be understood that the examples provided herein are illustrative and are not to be construed as limiting the scope of this invention in any way to the specific embodiments recited herein.

EXAMPLE 1

2,2'-[[3,6-Bis[2-(1-piperidinyl)ethoxy]-4,5-acridinediyl]-bis(methylene)]bis-1H-isoindol-1,3(2H)-dione, sulfate (2:5)

A suspension of 3,6-bis(2-chloroethoxy)acridine hydrochloride in piperidine was heated in a steel bomb at 80° C. for 24 hours. The excess piperidine was removed in vacuo and the residual solution was washed twice with 30 ml portions of saturated aqueous sodium bicarbonate and filtered. The filtrate was evaporated to a residue, giving 3,6-bis(2-piperidinoethoxy)acridine as yellow crystals, mp 129°-130° C.

A 7.9 g portion of 3,6-bis(2-piperidinoethoxy)acridine was dissolved in 50 ml of concentrated sulfuric acid at 40° C. To this was added 6.5 g of hydroxymethyl phthalimide at 35° C. and the mixture was allowed to stand 17 hours at room temperature. An additional 1.1 g of hydroxymethyl phthalimide was added, the mixture was warmed to 40° C. then allowed to stand for 1.5 hours. The mixture was then poured onto ice, the resulting crystals were collected, dissolved in 200 ml of hot water and then cooled in an ice bath. The crystals were collected and washed with isopropanol, giving 13.8 g of the desired product, mp 190°-205° C.

EXAMPLE 2

3,6-Bis[2-(diethylamino)ethoxy]-4,5-acridinedimethanol

To a solution of 23.43 g of 3,6-bis(2-diethylaminoethoxy)acridine trihydrochloride (U.S. Pat. No. 3,740,403) in 85 ml of concentrated sulfuric acid was added 2.94 g of paraformaldehyde. The mixture was stirred 45 minutes, then added to 1.5 liters of ether. The resulting solid was collected, dissolved in water, sodium bicarbonate was added and the mixture extracted with six 75 ml portions of chloroform. These extracts were placed on an alumina column which was then eluted with ether and then methylene chloride. The methylene chloride extract was concentrated, giving 4.0 g of the desired product as yellow crystals, mp 95°–96° C.

EXAMPLE 3

2,2′-[[3,6-Bis[2-(diethylamino)ethoxy]-4,5-acridinediyl]-bis(methylene)]bis-1H-isoindol-1,3(2H)-dione To a solution of 15.72 g of 3,6-bis(2-diethylaminoethoxy)acridine trihydrochloride in 70 ml of concentrated sulfuric acid was added 11.0 g of hydroxymethyl phthalimide. The mixture was allowed to stand 18 hours and then poured onto ice. The resulting solid was collected, dissolved in hot chloroform, dried and concentrated. The resulting yellow crystals were collected and washed with ether, giving 14 g of the desired product, mp 242°–244° C.

EXAMPLE 4

3,6-Bis[2-(diethylamino)ethoxy]-4,5-acridinedimethanamine, tetrahydrochloride

A solution of 1.52 g of 2,2′-[[3,6-bis[2-(diethylamino)ethoxy]-4,5-acridinediyl]bis(methylene)]bis-1H-isoindol-1,3(2H)-dione, 40 ml of ethanol and 1.4 ml of hydrate was refluxed for 3 hours, cooled and filtered. The filtrate was concentrated, refiltered and to this filtrate was added sodium hydroxide. The resulting gummy orange solid was dissolved in chloroform, concentrated, isopropanol and hydrochloric acid were added and the resulting solid collected, dissolved in hot methanol and cooled, giving 593 mg of the desired product, mp 271°–280° C. (dec.).

EXAMPLE 5

3,6-Bis[2-(diethylamino)ethoxy]-4,5-diformylacridine

To a solution of 0.469 g of 3,6-bis[2-(diethylamino)ethoxy]-4,5-acridinedimethanol in a mixture of 5.0 ml of anhydrous dimethyl sulfoxide and 2.8 ml of triethylamine is added a solution of 0.96 g of sulfur trioxide-pyridine complex in 5 ml of anhydrous dimethyl sulfoxide. The reaction mixture is stirred at room temperature for one hour. Most of the dimethyl sulfoxide is removed under reduced pressure without heat. The residue is treated first with 50 ml of saturated sodium bicarbonate solution and then with 50 ml of water, giving 0.35 g of the desired product as a yellow solid.

We claim:

1. A compound of the formula:

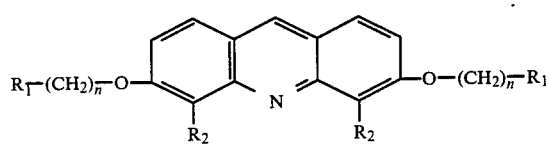

wherein n is an integer 2 or 3; $R_1$ is selected from the group consisting of piperidinyl, $-N[alkyl(C_1-C_5)]_2$, pyrrolidino and morpholino; $R_2$ is selected from the group consisting of formyl, hydroxymethyl, aminomethyl and

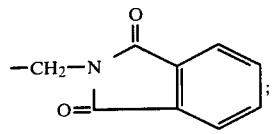

and the pharmaceutically acceptable salts thereof.

2. A compound of the formula:

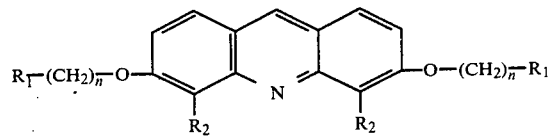

wherein $R_1$ is selected from the group consisting of piperidinyl and $-N[C_2H_5]_2$; $R_2$ is selected from the group consisting of formyl, hydroxymethyl, aminomethyl and

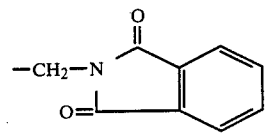

and the pharmaceutically acceptable salts thereof.

3. The compound as recited of claim 1 or 2, 2,2′-[[3.6-bis[2-(1-piperidinyl)ethoxy]-4,5-acridinediyl]bis(methylene)bis-1H-isoindol-1,3(2H)dione.

4. The compound as recited in claim 1 or 2, 3,6-bis(-diethylamino)ethoxy]-4,5-acridinedimethanol.

5. The compound as recited in claim 1 or 2, 2,2′-[[3,6-bis[2-(diethylamino)ethoxy]-4,5-acridinediyl]bis(methylene)]bis-1H-isoindol-1,3(2H)-dione.

6. The compound as recited in claim 1 or 2, 3,6-bis[-(diethylamino)ethoxy]-4,5-acridinedimethanamine.

7. The compound as recited in claim 1 or 2, 3,6-bis[2-(diethylamino)ethoxy]-4,5-diformylacridine.

8. A method of restoring, stimulating or enhancing the immune system in a warm-blooded animal which comprises administering to said animal an effective amount of a compound of the formula as recited in claim 1 and the pharmaceutically acceptable salts thereof.

9. A method of restoring, stimulating or enhancing the immune system in a warm-blooded animal which comprises administering to said animal an effective amount of a compound of the formula as recited in claim 1 and the pharmaceutically acceptable salts thereof in association with a pharmaceutically acceptable carrier, adjuvant or diluent.

10. The method of restoring, stimulating or enhancing the immune system in a warm-blooded animal which comprises administering to said animal an effective amount of a compound of the formula as recited in claim 2 and the pharmaceutically acceptable salts thereof.

11. A method of restoring, stimulating or enhancing the immune system in a warm-blooded animal which comprises administering to said animal an effective amount of a compound of the formula as recited in claim 2 and the pharmaceutically acceptable salts thereof in association with a pharmaceutically acceptable carrier, adjuvant or diluent.

12. The method of restoring, stimulating or enhancing the immune system in a warm-blooded animal as recited in claim 8, 9, 10 or 11 wherein the compound is 2,2'-[[3,6-bis[2-(1-piperidinyl)ethoxy]-4,5-acridinediyl]-bis(methylene)]bis-1H-isoindol-1,3(2H)-dione.

13. The method of restoring, stimulating or enhancing the immune system in a warm-blooded animal as recited in claim 8, 9, 10 or 11 wherein the compound is 3,6-bis[2-(diethylamino)ethoxy]-4,5-acridinedimethanol.

14. The method of restoring, stimulating or enhancing the immune system in a warm-blooded animal as recited in claims 8, 9, 10 or 11 wherein the compound is 2,2'-[[3,6-bis[2-(diethylamino)ethoxy]-4,5-acridinediyl]-bis(methylene)]bis-1H-isoindol-1,3(2H)-dione.

15. The method of restoring, stimulating or enhancing the immune system in a warm-blooded animal as recited in claims 8, 9, 10 or 11 wherein the compound is 3,6-bis[2-(diethylamino)ethoxy]-4,5-acridinedimethanamine.

16. The method of restoring, stimulating or enhancing the immune system in a warm-blooded animal as recited in claims 8, 9, 10 or 11 wherein the compound is 3,6-bis[2-(diethylamino)ethoxy]-4,5-diformylacridine.

17. A process for producing a compound of the formula:

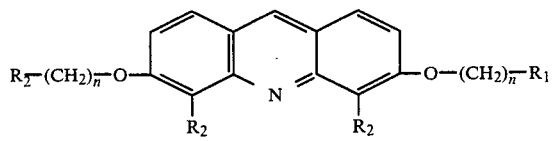

wherein n is an integer 2 or 3; $R_1$ is selected from the group consisting of piperidinyl, —N[alkyl($C_1$–$C_5$)]$_2$, pyrrolidino and morpholino; and $R_2$ is selected from the group consisting of formyl and hydroxymethyl which comprises reacting a 3,6-bis(substituted)acridine of the formula:

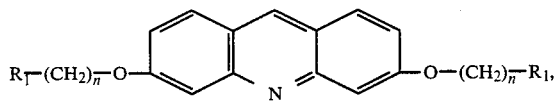

wherein n and $R_1$ are as described above, in concentrated sulfuric acid with paraformaldehyde for about ½ to about one hour; adding ether to yield compounds of the formula:

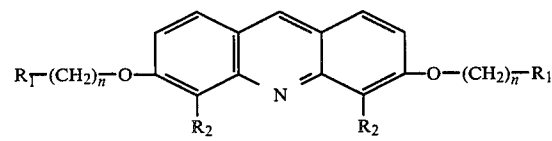

wherein $R_2$ is —CH$_2$OH; dissolving said compounds in dimethylsulfoxide; adding triethylamine; and reacting with sulfur trioxide-pyridine complex for about 1 to about 4 hours to yield the compounds of the above formula wherein n and $R_1$ are as described above and $R_2$ is formyl.

18. A process for producing a compound of the formula:

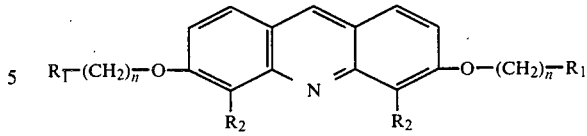

wherein n is an integer 2 or 3; $R_1$ is selected from the group consisting of piperidinyl, —N[alkyl($C_1$–$C_5$)]$_2$, pyrrolidino and morpholino; and $R_2$ is selected from the group consisting of aminomethyl and

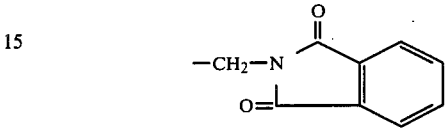

which comprises reacting a 3,6-bis(substituted)acridine of the formula:

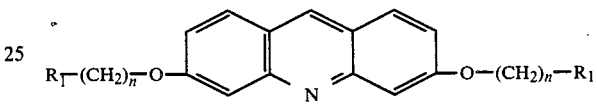

wherein n and $R_1$ are as described above, in concentrated sulfuric acid with hydroxymethyl phthalimide for about 12 to about 24 hours, to yield compounds of the formula:

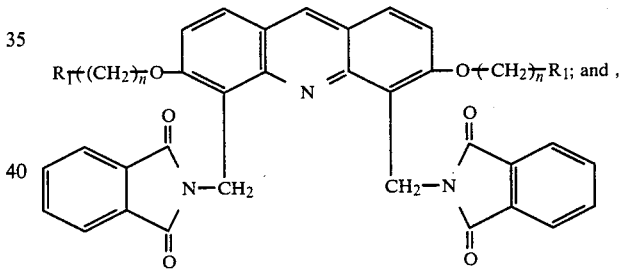

recovering said compounds or, if desired, reacting said compounds with hydrazine hydrate in ethanol at reflux for about 2 to about 4 hours to yield compounds of the formula:

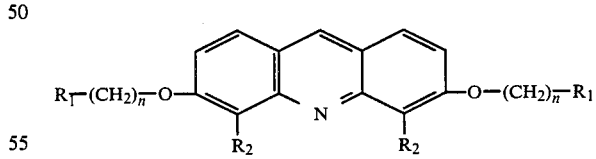

wherein n and $R_1$ are as described above and $R_2$ is aminomethyl.

19. An immunoenhancing method which comprises administering a compound as claimed in claim 1 in an effective amount to a warm-blooded animal having an immunity-associated disease.

20. An immunoenhancing method which comprises administering a compound as claimed in claim 1 in association with a pharmaceutically acceptable carrier, adjuvant or diluent in an effective amount to a warm-blooded animal having an immunity-associated disease.

* * * * *